United States Patent [19]

Patchett et al.

[11] 4,347,375

[45] Aug. 31, 1982

[54] PROCESS FOR PREPARING AMINO ACIDS AND ESTERS

[75] Inventors: Arthur A. Patchett, Westfield, N.J.; William J. Greenlee, New York, N.Y.

[73] Assignee: Merck & Co., Inc., Rahway, N.J.

[21] Appl. No.: 212,383

[22] Filed: Dec. 3, 1980

Related U.S. Application Data

[60] Division of Ser. No. 64,348, Aug. 6, 1979, Pat. No. 4,275,220, which is a continuation of Ser. No. 927,209, Jul. 24, 1978, abandoned.

[51] Int. Cl.³ .................. C07D 233/64; C07C 101/30
[52] U.S. Cl. .......................... 548/344; 260/326.14 T; 560/40; 560/155; 560/169; 560/171; 560/172
[58] Field of Search .................. 560/40, 39, 169, 171, 560/155, 172; 548/344; 260/326.14 T

[56] References Cited

U.S. PATENT DOCUMENTS 3,718,688  2/1973  Davis .................................. 560/40
4,147,873  4/1979  Metcalf et al. ...................... 560/39
4,182,891  1/1980  Metcalf et al. ...................... 560/39

Primary Examiner—G. T. Breitenstein
Attorney, Agent, or Firm—Daniel T. Szura; Harry E. Westlake, Jr.

[57] ABSTRACT

A process for preparing α-amino acids or ester thereof having an α-vinyl substituent and certain intermediates are disclosed.

7 Claims, No Drawings

PROCESS FOR PREPARING AMINO ACIDS AND ESTERS

This is a division of Ser. No. 064,348, filed Aug. 6, 1979, now U.S. Pat. No. 4,275,220 issued June 23, 1981, which is a continuation of application Ser. No. 927,209, filed July 24, 1978, now abandoned.

BACKGROUND OF THE DISCLOSURE

The present invention is concerned with an efficient process for preparing α-vinyl substituent-α-amino acids and esters and certain intermediates.

Cerain α-vinyl-α-amino acids can be prepared by reducing the corresponding α-ethynyl α-amino acid. Such processes are described in Tetrahedron Lett. 2745–2748; 3689–3692 (1977).

A more efficient process for preparing α-vinyl-α-amino acids and esters has been discovered.

SUMMARY OF THE INVENTION

A process for preparing α-vinyl-α-amino acids and esters thereof from a novel intermediate of the formula:

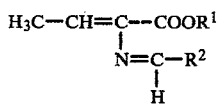

DESCRIPTION OF THE PREFERRED EMBODIMENTS

An embodiment of the present invention is a process for preparing compounds having the formula:

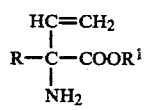

which comprises (a) treating a compound of the formula:

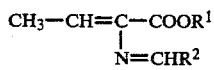

with a strong amine base, (b) reacting the product from (a) with an alkylating agent,

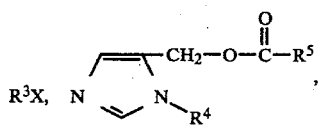

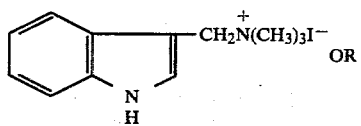

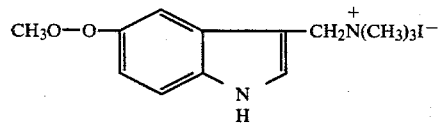

and (c) hydrolyzing the product from (b), wherein R is alkyl, alkenyl or substituted alkyl, $R^1$ is H or lower alkyl, $R^2$ is the residue of an aldehyde $R^2CHO$, $R^3$ is alkyl, alkenyl or substituted alkyl, $R^4$ is alkyl-; substituted alkyl- or aryl sulfonyl, $R^5$ is alkyl, aryl or alkaryl and X is Cl, Br or I.

R is an alkyl, substituted alkyl or alkenyl group. Preferred R substituents are selected from the group consisting of:

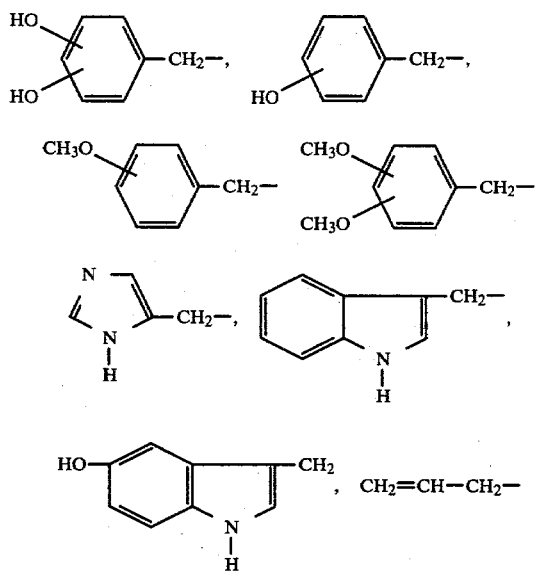

$CH_3-OOC-CH_2-$, $(CH_3)_2-CH-$
$HOOC-CH_2-$ AND $H_2N-CH_2-CH_2-CH_2-$

Especially preferred R groups are:

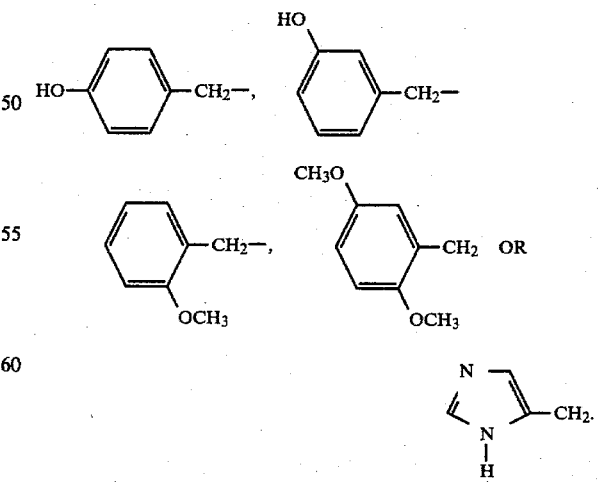

$R^1$ is a lower $C_1-C_8$, alkyl group, such as octyl, hexyl, pentyl, isopropyl, ethyl or methyl. Preferred $R^1$ groups are $C_1-C_6$ alkyl. A most preferred $R^1$ group is methyl.

$R^2$ is the residue of an aldehyde formula $R^2$ CHO, having no α-hydrogen, where $R^2$ is a phenyl or substituted phenyl group wherein the substituents are halo (Cl, Br or I) $C_1$-$C_3$ alkyl or $NO_2$. Examples of specific $R^2$ groups are phenyl, p-chlorophenyl, 4-nitrophenyl, 4-isopropylphenyl and the like. A preferred $R^2$ group is phenyl.

$R^3$ is an alkyl, alkenyl or substituted alkyl group which is the same as or readily convertible to the R group. Readily convertible $R^3$ groups are R groups which bear OH groups and are protected. Examples of such protected moieties are:

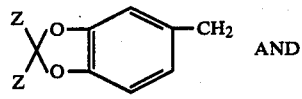
AND
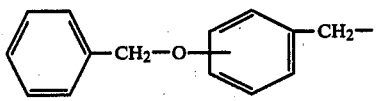

Z is H, lower alkyl e.g. $CH_3$ or butyl, phenyl or substituted phenyl e.g. p-$CH_3$-phenyl. A preferred Z group is phenyl.

$R^4$ is an alkyl, substituted alkyl or aryl sulfonyl group such as p-toluenesulfonyl, benzenesulfonyl, nitrophenylsulfonyl, chloraphenylsulfonyl, hexylsulfonyl, and the like.

X is halo e.g. Br, Cl or I. Chloro is preferred.

$R_5$ is a $C_1$-$C_5$ alkyl group e.g. $CH_3$, pentyl or isopropyl; an aryl group such as phenyl, bromophenyl, p-totyl, xylyl and the like; an ararkyl group such as benzyl and the like. A preferred $R_5$ group is the $C_1$-$C_5$ arkyl moiety, expecially methyl.

The process of the present invention is illustrated by the following reaction equation sequence when Ph is phenyl:

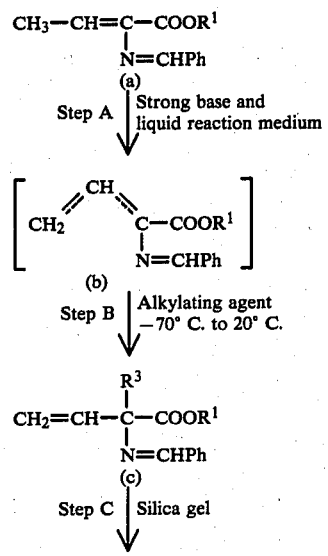

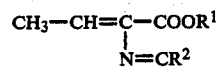

The Schiff base (a) is conveniently prepared from β-chloro-α-amino butyric methyl ester hydrochloride using the process described in Helv. Chem Acta 40, 1531 (1957).

The strong base in Step A may be a suitable lithium dialkylamide. Examples of such bases are lithium diisopropylamide, lithium dimethylamide, lithium dicyclohexylamide and the like and lithium hexamethyldisilazide. A preferred base is lithium hexamethyldisilazide.

The liquid reaction medium used for step A is preferably an aprotic medium such as hexamethylphosphoramide (HMPA)m tetrahydrofuran (THF), ethyl ether 1.4-dioxane and the like. A preferred medium is HMPA and THF.

Step A is carried out at temperatures ranging from about −70° C. to about room temperature.

Intermediate (b) amine is not ordinarily isolated and step B is carried out on directly on the step A reaction product.

In step B, the (b) is treated with an appropriate alkylating agent as defined above. The alkylating agent is added directly to the reaction product (b) in said liquid reaction medium. Step B is carried out at temperatures ranging from about 70° C. to room temperature.

The =CH—$R^2$ amine blocking group is removed from reaction product (c) using conventional technology e.g. by passing the reaction product through a column of acidified silica gel.

The ester (d) is then hydrolyzed using a suitable inorganic acid to produce the final product (e) as the acid salt. The hydrolysis step also serves to remove any other blocking groups, e.g., the hydroxyl blocking group present in the $R^3$ moiety.

The final product (e) may be converted to the free base by conventional neutralization.

Another embodiment of the present invention is the intermediate of the formula:

$$CH_3-CH=\underset{N=CR^2}{\overset{}{C}}-COOR^1$$

where $R^1$ and $R^2$ are defined as above. A preferred intermediate has the formula:

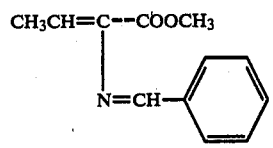

The Formula I products have pharmaceutical activity, e.g., as enzyme inhibitors, antihypertensive agents, antitumor agents, antiallergics and the like.

The following examples illustrate the process of the present invention. All temperatures are in degrees Celsius.

EXAMPLE I (A) N-benzylidine-2-aminocrotonic acid methyl ester

To a well-stirred slurry of 16.6 g of (DL)-$\beta$-chloro-$\alpha$-amino-butyric acid methyl ester hydrochloride in 160 ml of methylene chloride was added at 5° C., 9.0 ml of benzaldehyde, 7.5 g of anhydrous magnesium sulfate and 12.3 ml of triethylamine. After 20 hours the reaction mixture was diluted with 200 ml of water and the layers were separated. After three extractions of the aqueous layer with 100 ml of methylene chloride, the combined organic portions were washed with brine and dried with 5 g of anhydrous magnesium sulfate, giving after evaporation of solvent 20.8 g of crude (DL)-N-benzylidine-$\beta$-chloro-$\alpha$-aminocrotonic acid methyl ester. This was dissolved in 160 ml of methylene chloride, and 13.0 ml of 1,5-diazabicyclo [5.4.0] undec-5-ene was added with stirring to the cooled (5° C.) solution. After 90 minutes the reaction mixture was washed with 100 ml of water, then dried with 10 g of anhydrous sodium sulfate. The residue after evaporation of solvent was filtered through neutral alumina (70 g) in 10:1 hexane:ether, providing 14.5 g of pure N-benzylidine-2-aminocrotonic acid methyl ester as a 60:40 mixture of E:Z isomers. NMR (CDCl$_3$) showed: E isomer; 2.00 (3H,d,J=7), 3.77 (3H,s), 5.88(1H,q,J=7), 8.18(1H,s), 7.1–7.8 (5H,m); Z isomer; 1.83 (3H,d,J=7), 3.73 (3H,s), 6.50 (1H,q,J=7), 8.40 (1H,s), 7.1–7.8 (5H,m). TLC showed overlapping spots, R$_f$=0.3 (silica gel, 5:1 hexane:ether). IR (CHCl$_3$) showed 1720, 1660, 1575 cm$^{-1}$. Mass Spectrum, Calcd. for C$_{12}$H$_{13}$NO$_2$, 203.0946 Found: 203.0946.

(B) Benzyloxy-$\alpha$-vinyltyrosine methyl ester

A solution of lithium hexamethyldisilazide was prepared by adding 5.5 mmol of butyllithium (2.2 M solution in hexane) to a cooled (−70° C.) solution of 1.15 ml of hexamethyldisilazane in 12.5 ml of tetrahydrofuran. To this solution was added first 3.5 ml of hexamethylphosphoramide and then a solution of 1.15 g of N-benzylidine-2-aminocrotonic acid methyl ester in 12.5 ml of tetrahydrofuran. After 45 minutes, a solution of 1.385 g of p-benzyloxybenzyl bromide in 7.5 ml of tetrahydrofuran was added. Stirring was continued for one hour at −70° C. and then for two hours at room temperature. The reaction mixture was diluted with saturated ammonium chloride solution and extracted three times with 50 ml of ether. The combined organic portions were washed twice with water and once with brine and dried with anhydrous magnesium sulfate. The residue upon removal of solvent was dissolved in 5 ml of methylene chloride and placed onto a column of acid-washed silica gel (25 g of silica gel 60, E. Merck cat. no. 7736, previously washed with 6 N hydrochloric acid, water to neutrality, saturated disodium EDTA solution, water, and then 0.3 N hydrochloric acid and dried in air for 72 hours, was slurrypacked in hexane). Elution was carried out under a positive pressure of nitrogen with hexane (100 ml), ether (100 ml), 10:1 ether: acetonitrile (150 ml), and 100:10:2 ether: acetonitrile:triethylamine. The last solvent mixture brought about elution of 1.206 g of benzyloxy-$\alpha$-vinyltyrosine methyl ester. NMR (CDCl$_3$) showed: 1.57 (2H, broad s), 3.13 (2H,AB, J$_{AB}$=14, $\delta_{AB}$=30), 3.62 (3H,s), 4.92 (2H,s), 5.07 (1H,d of d, J=10,1), 5.22 (1H, d of d, J=17,1), 6.08 (1H, d of d, J=17,10), 7.20 (4H,AB,J$_{AB}$=9, $\delta_{AB}$=14), 7.3–7.5 (5H,m). IR (CHCl$_3$) 3400, 1730 cm$^{-1}$.

EXAMPLE 2

Following the procedure of Example 1B), 1.385 g of m-benzyloxybenzyl bromide was used in place of the p-benzyloxybenzyl bromide, to prepare 1.020 g of benzyloxy-$\alpha$-vinyl-m-tyrosine methyl ester. m/e Calcd for C$_{19}$H$_{21}$NO$_3$: 311.1520 Found: 311.1519.

EXAMPLE 3

Following the procedure of Example 1B), 0.850 g of 2-iodopropane was used in place of the p-benzyloxybenzyl bromide, to prepare 0.620 g of $\alpha$-vinylvaline methyl ester. m/e 157

EXAMPLE 4

Following the procedure of Example 1B), 0.665 g of allyl bromide was used in place of the p-benzyloxybenzyl bromide, to prepare 0.591 g of $\alpha$-allyl-$\alpha$-vinylglycine methyl ester. m/e 155.

EXAMPLE 5

Following the procedure of Example 1B), 0.765 g of methyl bromoacetate was used in place of the p-benzyloxybenzyl bromide, to prepare 0.679 g of $\alpha$-vinylaspartic acid dimethyl ester. m/e 187

EXAMPLE 6

Following the procedure of Example 1B), 1.127 g of 3,4-diphenylmethylenedioxybenzyl bromide was used in place of the p-benzyloxybenzyl bromide, to prepare 0.990 g of 3,4-diphenylmethylenedioxybenzyl-$\alpha$-vinyl glycine methyl ester m/e Calcd for C$_{25}$H$_{23}$NO$_4$: 401.1626 Found: 401.1629.

EXAMPLE 7

Following the procedure of Example 1B), 1.470 g of N-tosylacetoxymethylimidazole was used in place of the p-benzyloxybenzyl bromide, to prepare 1.301 g of $\alpha$-N-tosylimidazoylmethyl-$\alpha$-vinylglycine methyl ester. m/e 351.

EXAMPLE 8

Following the procedure of Example 1B), o-methoxybenzyl bromide is used in place of the p-benzyloxybenzyl bromide, to prepare methoxy-$\alpha$-vinyl-o-tyrosine methyl ester.

EXAMPLE 9

Following the procedure of Example 1B), 2,5-dimethoxybenzyl bromide is used in place of the p-benzyloxybenzyl bromide to prepare 2,5-dimethoxybenzyl-$\alpha$-vinylglycine methyl ester.

EXAMPLE 10

Following the procedure of Example 1B), N-benzylidine-3-amino-1-bromopropane in used in place of the p-benzyloxybenzyl bromide to prepare $\alpha$-vinylornithine methyl ester.

EXAMPLE 10a

Following the procedure of Example 1B), gramine methiodide is used in place of the p-benzyloxybenzyl bromide to prepare α-vinyltryptophan methyl ester.

EXAMPLE 11

α-Vinyltyrosine hydrochloride

A mixture consisting of 0.554 g of benzyloxy-α-vinyltyrosine methyl ester and 40 ml of 6 N aqueous hydrochloric acid was heated at reflux with rapid stirring for 2 hours. The reaction mixture was cooled, extracted three times with 5 ml of methylene chloride and treated with activated charcoal. Filtration and evaporation of solvent gave 0.355 g of α-vinyltyrosine hydrochloride as an amorphous solid. NMR (D$_2$O) showed: 3.35 (2H,AB, J$_{AB}$=15, δ$_{AB}$=22), 5.55 (1H,d, J=18), 5.70 (1H,d,J=12), 6.43 (1H, d of d, J=18,12), 7.27 (2H,AB, J$_{AB}$=9, δ$_{AB}$=22). m/e 207 (P-36).

EXAMPLE 12

Using 0.885 g of benzyloxy-α-vinyl-m-tyrosine methyl ester in place of the benzyloxy-α-vinyltyrosine methyl ester in the Example 11 procedure, 0.552 g of α-vinyl-m-tyrosine hydrochloride, [m/e 207 (P-36)], were obtained.

EXAMPLE 13

Using 0.253 g of α-vinylvaline methyl ester in place of the benzyloxy-α-vinyltyrosine methyl ester in the Example 11 procedure, 0.191 g of α-vinylvaline hydrochloride were obtained: NMR (D$_2$O): 0.95 and 0.97 δ(3H,d,J=7), 2.35 (1H,septet,J=7), 5.27 (1H,d,J=18), 5.45 (1H,d,J=11), 6.12 (1H,d of d, J=18,11).

EXAMPLE 14

Using 0.580 g of α-allyl-α-vinylglycine methyl ester in place of the benzyloxy-α-vinyltyrosine methyl ester in the Example 11 procedure, 0.626 g of α-allyl-α-vinylglycine hydrochloride [m/e 142 (P-35)] were obtained.

EXAMPLE 15

Using 0.565 g of α-vinylaspartic acid dimethyl ester in place of the benzyloxy-α-vinyltyrosine methyl ester in the Example 11 procedure, 0.571 g of α-vinylaspartic acid hydrochloride were obtained. NMR (D$_2$O) 3.00 (2H,AB, J$_{AB}$=18, δ$_{AB}$22), 5.20 (1H,d, J=19), 5.28 (1H,d, J=10), 5.78 (1H,d of d,J=19,10).

EXAMPLE 16

Using 0.250 g of 3,4-diphenylmethylenedioxybenzyl-α-vinylglycine methyl ester in place of the benzyloxy-α-vinyltyrosine methyl ester in the Example 11 procedure, 0.150 g of α-vinyl DOPA hydrochloride were obtained. m/e 223 (P-36)

EXAMPLE 17

A mixture of 1.301 g of α-N-tosylimidazoylmethyl-α-vinylglycine methyl ester and 15 ml of concentrated hydrochloric acid was heated at reflux for 5 hours. The reaction mixture was cooled, extracted three times with 5 ml of methylene chloride, and treated with activated charcoal. Filtration and evaporation of solvent, and then purification by ion-exchange chromatography ① gave 0.695 g of α-vinylhistidine dihydrochloride as an amorphous solid. NMR (D$_2$O) showed: 3.42 (2H,s), 5.32 (1H,d, J=16), 5.48 (1H, d, J=10), 6.05 (1H, d of d, J=16,10), 7.28 (1H, d, J=1), 8.52 (1H,d, J=1). TLC showed a single spot, R$_f$=0.3 (silica gel, 50:8:20 butanol:acetic acid:water).

① on Dowex 50W-X4 cation exchange resin.

EXAMPLE 18

Using the Example 17 procedure, methoxy-α-vinyl-o-tyrosine methyl ester is treated to give o-methyl-α-vinylphenylalanine.HCl.

EXAMPLE 19

Using the Example 17 procedure, 2,5-dimethoxybenzyl-α-vinylglycine methyl ester is treated to give 2,5-dimethoxy-α-vinylphenylalanine hydrochloride.

EXAMPLE 20

Using the procedure of Example 1B, alkylation was carried out with N-benzylidine-3-amino-1-bromopropane. After workup with aqueous ammonium chloride as described, the crude product was mixed with 100 ml. of 6 N hydrochloric acid and the well-stirred mixture was heated at 110° C. for 2 hours. The solution was cooled, extracted four times with 10 ml. of methylene chloride, and treated with activated charcoal. The solution was filtered and evaporated, and the residue purified on DOWEX 50W-X4 cation exchange resin, eluted first with water and then with 2 N hydrochloric acid, giving 0.560 g. of α-vinylornithine dihydrochloride as a white foam. NMR (D$_2$O) showed: 1.4–2.2 δ(4H,m), 2.8–3.1 (2H,m), 5.15 (1H,d,J=18), 5,25 (1H,d,J=10), 5.87 (1H,d of d,J-18,10).

EXAMPLE 21

α-Vinyltryptophan

Treatment of α-vinyltryptophan methyl ester in 1.1 methanol:water with two equivalents of sodium hydroxide, neutralization of the reaction mixture with 1 N aqueous hydrochloric acid, and purification of the crude amino acid on DOWEX 50W-X4 cation exchange resin (elution with water and then 2 N aqueous hydrochloric acid) gives α-vinyltryptophan hydrochloride.

EXAMPLE 22

The procedure described in Example 2 is carried out except that 5-methoxymethylgramine methiodide (5 mmol) is used in place of p-benzyloxybenzyl bromide and that the crude product is not submitted to the silica gel treatment but is instead dissolved in 1:1 methanol:water (50 ml.) and treated with two equivalents of potassium hydroxide. After five hours, the reaction mixture is acidified to pH=3 by addition of 1 N hydrochloric acid and the resulting solution is refluxed for 5 minutes. The reaction mixture is cooled, just neutralized with aqueous potassium bicarbonate, and concentrated to dryness under vacuum. Purification of the crude amino acid on DOWEX 50W-X4 cation exchange resin (elution with water and then 2 N aqueous hydrochloric acid) gives 5-hydroxy-α-vinyltryptophan hydrochloride.

Claims to the invention follow.

What is claimed is:

1. A process for preparing compounds having the formula:

$$\begin{array}{c} HC=CH_2 \\ | \\ R-C-COOR^1 \\ | \\ NH_2 \end{array}$$

which comprises (a) treating a compound of the formula:

$$\begin{array}{c} CH_3-CH=C-COOR^1 \\ | \\ N=CHR^2 \end{array}$$

with a strong amine base, (b) reacting the product from (a) with an alkylating agent selected from the group consisting of:

$R^3X$,

[structure: imidazoline-type ring with $-CH_2-O-\overset{O}{\underset{\|}{C}}-R_5$, containing N and N-R$^4$],

[indole structure with $-CH_2-\overset{+}{N}(CH_3)_3\overline{I}$] or

[indole with $CH_3O-CH_2O-$ substituent and $-CH_2-\overset{+}{N}(CH_3)_3\overline{I}$]

and (c) hydrolyzing the product from (b), wherein R is alkyl, alkenyl or substituted alkyl selected from a group consisting of:

[dihydroxyphenyl-CH$_2$–], [hydroxyphenyl-CH$_2$–],

[methoxyphenyl-CH$_2$–], [dimethoxyphenyl-CH$_2$–],

[imidazole-CH$_2$–], [indole-CH$_2$–],

[hydroxyindole-CH$_2$–], $CH_3-OOC-CH_2-$, $HOOC-CH_2-$ and $H_2N-CH_2-CH_2-CH_2$, $R^1$ is lower alkyl, $R^2$ is the residue of an aldehyde $R^2CHO$ having no α-hydrogen where $R^2$ is a phenyl or substituted phenyl group wherein the substituents are Cl, Br, I, $C_1-C_3$ alkyl or $NO_2$, $R^3$ is alkyl, alkenyl substituted alkyl selected from the group consisting of:

[dihydroxyphenyl-CH$_2$–], [hydroxyphenyl-CH$_2$–],

[methoxyphenyl-CH$_2$–], [dimethoxyphenyl-CH$_2$–],

[imidazole-CH$_2$–], [indole-CH$_2$–],

[hydroxyindole-CH$_2$–], $CH_3-OOC-CH_2-$, $HOOC-CH_2-$, $H_2N-CH_2-CH_2-CH_2-$,

[benzodioxole with Z,Z substituents and $-CH_2$] and

[PhCH$_2$O-phenyl-CH$_2$O-phenyl-CH$_2$]

wherein Z is H, lower alkyl, phenyl or substituted phenyl, $R^4$ is alkyl or aryl sulfonyl wherein said aryl-sulfonyl is p-toluenesulfonyl, benzenesulfonyl, nitrophenylsulfonyl or chlorophenyl sulfonyl, and $R^5$ is alkyl, aryl or alkaryl and X is Cl, Br or I.

2. The process of claim 1 wherein said amine base is lithium hexamethyldisilazide.

3. The process of claim 2 wherein $R^2$ is phenyl.

4. The process of claim 3 wherein said (b) reactant is $R^3X$.

5. The process of claim 4 wherein $R^3$ is:

[Ph,Ph-benzodioxole-CH$_2$–],

[PhCH$_2$O-phenyl-CH$_2$–], $CH_2=CH-CH_2-$, $CH_3-O-\overset{O}{\underset{\|}{C}}-CH_2-$, or $(CH_3)_2-CH-$.

wherein Ph is phenyl.

6. The process of claim 5 wherein $R^3$ is:

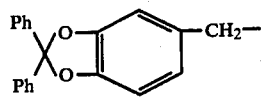
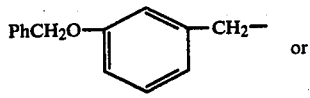 or
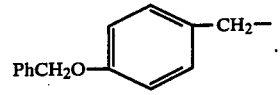
7. The process of claim 3 wherein said (b) reactant is:
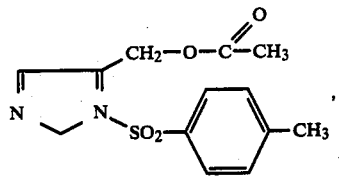
* * * * *